United States Patent [19]

Drake

[11] Patent Number: 4,609,637

[45] Date of Patent: Sep. 2, 1986

[54] CATALYSTS FOR DIMERIZATION AND PROCESS FOR PREPARING THE CATALYSTS

[75] Inventor: Charles A. Drake, Bartlesville, Okla.

[73] Assignee: Phillips Petroleum Company, Bartlesville, Okla.

[21] Appl. No.: 727,951

[22] Filed: Apr. 26, 1985

Related U.S. Application Data

[62] Division of Ser. No. 634,711, Jul. 26, 1984, Pat. No. 4,544,790.

[51] Int. Cl.$^4$ .................. B01J 23/04; B01J 23/72; B01J 23/78; B01J 27/20
[52] U.S. Cl. ..................... 502/174; 23/313 R
[58] Field of Search ............ 502/174, 345; 23/313 R; 264/117; 423/421

[56] References Cited

U.S. PATENT DOCUMENTS

| | | | |
|---|---|---|---|
| 2,994,725 | 8/1961 | Shaw et al. | 260/668 |
| 3,048,478 | 8/1962 | Smith | 23/313 |
| 3,175,020 | 3/1965 | Wilkes | 260/683.15 |
| 3,175,021 | 3/1965 | Vanselow et al. | 260/683.15 |
| 3,198,748 | 8/1965 | Keith et al. | 252/443 |
| 3,207,812 | 9/1965 | Hambling et al. | 260/683.15 |
| 3,325,559 | 6/1967 | Yeo et al. | 260/683.15 |
| 3,389,190 | 6/1968 | Alderson et al. | 260/683.15 |
| 3,424,814 | 1/1969 | Hambling et al. | 260/683.15 |
| 3,432,572 | 3/1969 | Tazuma et al. | 502/174 X |
| 3,463,618 | 8/1969 | Harris et al. | 23/313 |
| 3,689,587 | 9/1972 | Grebbell et al. | 260/683.15 E |
| 3,755,491 | 8/1973 | Hashimoto | 260/683.15 E |
| 3,853,786 | 12/1974 | Forni et al. | 252/440 |
| 3,916,019 | 10/1975 | Closson et al. | 260/683.15 E |
| 3,950,450 | 4/1976 | Hashimoto et al. | 260/683.15 E |
| 4,199,348 | 4/1980 | Ground | 264/117 X |
| 4,388,480 | 6/1983 | Imai et al. | 585/516 |

*Primary Examiner*—W. J. Shine
*Attorney, Agent, or Firm*—Stephen E. Reiter

[57] ABSTRACT

Catalysts and processes for the dimerization or co-dimerization of dimerizable olefins are provided. Catalysts consist essentially of at least one elemental alkali metal on one of several potassium carbonate-containing supports, optionally in the presence of at least one promoter selected from the group consisting of elemental copper, elemetal cobalt and finely divided stainless steel.

25 Claims, No Drawings

CATALYSTS FOR DIMERIZATION AND PROCESS FOR PREPARING THE CATALYSTS

This application is a divisional application of copending application, Ser. No. 634,711 filed July 26, 1984, now U.S. Pat. No. 4,544,790.

BACKGROUND

This invention relates to catalysts. In another aspect this invention relates to catalysts active for the dimerization of olefins. In yet another aspect, this invention relates to a process for the dimerization of olefins. In a further aspect, this invention relates to the preparation of catalysts.

It is known in the art to employ supported alkali metal catalysts for such conversions as propylene dimerization. In addition, the use of alkali metal carbonates as catalyst supports is known in the art. However, such catalysts as alkali metals supported on alkali metal carbonate supports do not always give high yields of the desired products, either due to low feed conversion, low product selectivity or both. In addition, the use of alkali metal carbonates alone as catalyst supports has been disadvantageous, especially in fixed bed operations for the reason that the supports do not have sufficient strength. Alternatively, prior art olefin dimerization catalyst systems have been limited to use in batch-type reaction due to the catalyst solubility or the fragile nature of prior art particulate catalysts.

OBJECTS OF THE INVENTION

It is therefore an object of this invention to provide catalysts and processes for the dimerization of dimerizable olefins with high selectivity and high yield.

It is another object of this invention to provide catalysts for the dimerization of dimerizable olefins which are well suited for use in fixed bed operation.

Yet another object of this invention is a method for the preparation of the above-mentioned catalysts.

These and other objects of the invention will become apparent from the disclosure and claims herein provided.

STATEMENT OF THE INVENTION

In accordance with the present invention, I have discovered that the addition of elemental copper to a dimerization catalyst consisting essentially of elemental alkali metal on potassium carbonate provides a novel catalyst which gives enhanced dimerization activity, i.e. improved feed olefin conversion and product selectivity.

Further in accordance with the present invention, I have discovered that the addition of finely divided stainless steel to a dimerization catalyst consisting essentially of elemental alkali metal on potassium carbonate surprisingly provides a novel catalyst with good dimerization activity which is rugged and useful, for example, in a fixed bed reactor.

Still further in accordance with the present invention, I have discovered novel supports for the preparation of rugged dimerization catalysts consisting essentially of elemental alkali metal on potassium carbonate which are well suited for the dimerization of olefins in a fixed bed reactor.

DETAILED DESCRIPTION OF THE INVENTION

Thus, in accordance with the present invention, a catalyst is provided consisting essentially of at least one elemental alkali metal, elemental copper and potassium carbonate.

In accordance with another embodiment of the invention, a catalyst consisting essentially of at least one elemental alkali metal, finely divided stainless steel and potassium carbonate is provided.

In accordance with yet another embodiment of the invention, there is provided a catalyst consisting essentially of at least one elemental alkali metal supported on a specially prepared potassium carbonate support, as well as a method for preparation of the support and catalyst.

In accordance with a further embodiment of the invention, a catalyst is provided consisting essentially of at least one elemental alkali metal, potassium carbonate and inorganic oxide support, wherein the potassium carbonate is melted onto the inorganic oxide support prior to adding at least one elemental alkali metal to the catalyst, as well as a method for catalyst preparation.

In accordance with a still further embodiment of the invention, a process is provided for treating dimerizable olefins with catalysts of the invention.

In accordance with one aspect of the invention, catalysts for the dimerization of dimerizable olefins are provided. Several different catalyst supports are contemplated to be within the scope of my invention.

Supports

Commercially available potassium carbonate in the form of a powder, pellets, granules or the like can be treated directly with at least one alkali metal and one or more of the desired promoting metals as discussed more fully below. This form of support has the advantage of being most readily obtained with a minimum of handling. In some circumstances, a large particle size and/or more rugged form of catalyst support is desired, such as, for example, where fixed bed reactions, especially large volume fixed bed reactions, are carried out.

Thus, in accordance with a particular embodiment of the invention, commercially available potassium carbonate is mixed with just enough water to form a thick paste. The thick paste is then oven dried under sufficient conditions of time and temperature to insure that substantially all water has been driven off. The dried paste is then broken up into pieces and fractionated by suitable means such as for example by passing through appropriate mesh size screen sieves to recover a desired particle size fraction. Although one skilled in the art of catalyst preparation can readily determine what ratios of potassium carbonate to water are suitable for the preparation of a thick paste, in order to provide guidance, it is suggested that a potassium carbonate/water weight ratio of at least about 3.5:1 be employed. The resulting catalyst support particles will be referred to hereinafter as "wet process" potassium carbonate support.

In accordance with another embodiment of the invention, commercially available potassium carbonate is (1) mixed with a non-acidic inorganic oxide support in a weight ratio of about 1:1 to about 1:10 potassium carbonate/inorganic oxide, (2) heated to at least about 950° C., (3) then cooled to about 80°–100° C. for treatment with one or more metals as discussed more fully below.

Catalyst support prepared in this manner will be referred to hereinafter as "melt process" potassium carbonate support.

The term "non-acidic inorganic oxide support" is intended to include those inorganic oxide materials which have low double bond isomerization activity under the reaction conditions employed for olefin dimerization. Suitable materials include but are not limited to alumina, silica, silica-alumina, magnesia-titania, thoria, magnesia, titania, zirconia and the like and mixtures of any two or more thereof. Alumina and silica-alumina are preferred because of their ready availability, ease of handling and resultant good catalyst activity.

In accordance with yet another embodiment of the invention, a potassium carbonate catalyst support with greatly improved physical integrity results when finely divided stainless steel in amounts of up to about 80 wt. % based on total catalyst weight is blended with potassium carbonate prior to or simultaneous with the treatment of support with one or more metals as discussed more fully below. Catalyst support prepared in this manner will be referred to hereinafter as "metal containing" potassium carbonate support.

The term "stainless steel" as used herein is intended to cover broadly those alloys of iron which are relatively inert to the reaction conditions employed for the dimerization of olefins. Contemplated materials include, but are not limited to type 303 stainless steel, type 316 stainless steel, type 410 stainless steel, type 431 stainless steel, Hastelloy C, and the like. Type 316 stainless steel is presently preferred because of its relatively low cost, ready availability, and resultant good catalyst activity.

Catalysts

Catalysts employed in the practice of this invention consist essentially of one of the potassium carbonate supports described above, at least one elemental alkali metal and optionally one or more of the following promoters:

elemental copper,
elemental cobalt,
finely divided stainless steel, and mixtures of two or more thereof. It should be recognized, however, that the catalysts of the invention can contain additional components which do not adversely affect the catalyst performance, such as, for example, pigments, dyes, processing aids, inert fillers, binders and the like.

The alkali metals contemplated to be within the range of the invention include lithium, sodium, potassium, rubidium and cesium. While the proportion of alkali metal combined with the potassium carbonate support can vary appreciably, generally at least about one weight percent of alkali metal based on the total weight of treated support will be employed. Generally, about 1 to about 20 wt. % alkali metal will be employed with about 2 to about 15 wt. % preferred. An alkali metal loading of about 3 to about 10 wt. % based on the total weight of treated support is most preferred for most efficient use of reagents, high catalyst activity and selectivity, ease of catalyst preparation and the like. Similarly, potassium is the preferred alkali metal due to its ready availability as well as ease and safety in handling.

The proportion of promoter combined with the potassium carbonate support can vary appreciably, but generally, when a promoter is used, at least one weight percent of that promoter based on the total weight of treated support will be employed. The following amounts are provided for additional guidance:

| Promoter | Loading, Wt. % | | |
| --- | --- | --- | --- |
|  | Broad | Intermediate | Preferred |
| Cu | 1–30 | 3–20 | 5–12 |
| Co | 1–50 | 3–25 | 5–15 |
| SS | 1–80 | 3–60 | 5–50 |

The general procedure for preparation of the catalysts of the invention involves heating the potassium carbonate support to about 250° C. in an inert atmosphere such as for example in a dry box maintained under $N_2$, Ar or the like. The heated support is allowed to cool slowly to about 80°–95° C. at which time at least one elemental alkali metal is added with vigorous stirring to ensure even distribution. While the alkali metal treated support is maintained at or above about 80° C., any promoter such as for example elemental copper, is gradually added while the treated catalyst is continuously stirred. Catalyst is then ready to be charged to the reactor.

As indicated by the variety of supports, alkali metal components and promoters included within the scope of the invention, numerous catalyst combinations are possible. Thus, for example, wet process potassium carbonate support can be treated with elemental potassium, elemental copper and elemental cobalt to provide an active and selective catalyst. Similarly, metal containing potassium carbonate support can be treated with elemental alkali metal, such as for example, potassium, only; or the same support can be treated with elemental potassium and the promoter elemental copper, or the same support can be treated with elemental potassium plus elemental copper plus elemental cobalt and so on. Additional combinations as would occur to one skilled in the art are also within the scope of this invention. Several possible combinations are described in detail in the examples which follow. The combination of support, alkali metal and promoter(s) which one may choose to employ will depend on a variety of variables such as for example, reactor configuration, reaction temperature and pressure, olefin feed employed, rate of olefin feed, conversions desired and the like.

Reactants

Reactants applicable for use in the process of the invention are olefinic compounds which can (a) self-react, i.e., dimerize, to give useful products such as, for example, the self-reaction of propylene gives 4-methyl-1-pentene; and/or (b) olefinic compounds which can react with other olefinic compounds, i.e., co-dimerize, to give useful products such as, for example, co-dimerization of ethylene plus propylene gives 1-pentene, co-dimerization of ethylene and 1-butene gives 3-methyl-1-pentene and so forth. As used herein, the term "dimerization" is intended to include "co-dimerization" as defined above.

Suitable dimerizable olefinic compounds are those compounds having from about 3 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as for example propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes and so forth; 3-methyl-1-butene, 2-methyl-2-butene, 3-methyl-1-pentene, 3-methyl-2-pentene, 4-methyl-1-pentene, 4-methyl-2-pentene, tetramethylethylene and the like; cyclopentene, cyclohexene, methylcyclopentene, methylcyclohexene, and the like and mixtures of any two or more thereof.

Suitable co-dimerizable olefinic compounds are those compounds having from about 2 to about 30 carbon atoms, including all the compounds contemplated within the scope of "dimerizable" olefinic compounds as indicated above. In addition, olefinic compounds which do not have at least one allylic hydrogen atom are also included within the scope of co-dimerizable olefins. Exemplary compounds in addition to those indicated above, include, but are not limited to ethylene, 3,3-dimethyl-1-butene, ditertiarybutyl ethylene and the like and mixtures of any two or more thereof.

The compounds indicated above as dimerizable olefinic compounds are capable of undergoing both self-reaction, i.e., dimerization, and cross-reaction, i.e., co-dimerization, with other members of the same group or with those compounds designated as co-dimerizable. The co-dimerizable compounds which do not have at least one allylic hydrogen may be capable of isomerization to form an olefin having an allylic hydrogen under the reaction conditions employed. If such isomerization is not possible, then those non-isomerizable, co-dimerizable compounds which do not have at least one allylic hydrogen must, however, be contacted with at least one of the "dimerizable" compounds in order to facilitate the desired co-dimerization reaction. In other words, the co-dimerizable compounds which do not have at least one allylic hydrogen atom and are not capable of isomerization to produce an olefin having at least one allylic hydrogen are therefore not capable of reacting with themselves under the reaction conditions employed for the dimerization reaction.

Reaction Conditions

The dimerization reaction of the invention can be carried out using either batch or continuous types of operation, although the catalysts of the invention are particularly well suited for continuous, i.e., fixed bed, operation. Suitable equipment such as for example autoclaves, tubular reactors and the like as are well known in the art can be employed. No special materials of construction are required so that steel, stainless steel, glass-lined reactors, or the like can be employed.

The reaction temperature can vary depending on the catalyst and feed(s) employed. Typically, a temperature range of about 50° to about 250° C. is suitable. Temperatures of about 80° to about 200° C. are preferred with a range of about 120° to about 160° C. most preferred because optimum reaction rates are obtained with minimum by-product formation.

The dimerization reaction can be carried out by contacting the dimerizable olefins with catalyst in the liquid phase or the gas phase, depending on the structure and molecular weight of the olefin, as well as reaction temperature and pressure employed. Pressure during the dimerization reaction can vary between wide limits. In general, higher pressures favor the progress of the reaction. Thus, pressures of atmospheric up to about 10,000 psig and higher are suitable. Preferably, pressures of about 100 to about 5,000 psig are employed, with pressures of about 1000 to about 4000 psig most preferred in order to achieve a good balance between reaction rate and minimize equipment and operating costs necessitated by very high reaction pressures.

If the reaction is carried out in the liquid phase, solvents or diluents for the reactants can be used. Saturated Aliphatic hydrocarbons, e.g., pentane, hexane, cyclohexane, dodecane; aromatic compounds, preferably those without an alpha-hydrogen (which would be capable of undergoing alkylation under the reaction conditions) such as benzene and chlorobenzene are suitable. If the reaction is carried out in the gaseous phase, diluents such as aliphatic hydrocarbons, for example methane, ethane and/or substantially inert gases, e.g., nitrogen, argon, can be present.

The contact time required for the dimerization reaction depends upon several factors such as for example the activity of the catalyst, temperature, pressure, structure of the reactants employed, level of conversion desired, and the like. The length of time during which the dimerizable olefinic compounds are contacted with catalyst can vary conveniently between about 0.1 seconds and about 24 hours although shorter and longer contact times can be employed. Preferably, times of about one minute to about 5 hours are employed. Where reaction is carried out in continuous fashion, it is convenient to express the reactant/catalyst contact time in terms of weight hourly space velocity (WHSV), i.e., the ratio of the weight of reactant which comes in contact with a given weight of catalyst per unit time. Thus, a WHSV of about 0.1 to about 10 will be employed. A WHSV of about 0.5 to about 5 is preferred, with about 1 to about 4 WHSV most preferred for optimum catalyst productivity.

Products

The olefinic products of the invention have established utility in a wide variety of applications such as for example as monomers for use in the preparation of homopolymers, copolymers, terpolymers, e.g., as the third component of ethylene-propylene terpolymers useful as synthetic elastomers, and the like.

A further understanding of the present invention and its advantages will be provided by reference to the following examples.

A. SUPPORT PREPARATION

Example I

Wet process $K_2CO_3$ (a) Sixty milliliters of water was added to 200 grams of potassium carbonate to form a paste. After drying this paste at about 110° C. for about 18 hours it was ground, sieved to 8–14 mesh and dried further for about 3 hours in a furnace at 250° C. This was designated as support WP-1.

(b) After mixing 60 milliliters with 200 grams of potassium carbonate to form a paste as in paragraph (a) above, an additional 21 grams of potassium carbonate was added portionwise to form a very thick paste. This was dried, ground, sieved to 8–14 mesh, and redried as in paragraph (a) above. This was designated as support WP-2.

(c) The same procedure was followed as in paragraph (b) above except that 25.6 grams instead of 21 grams of additional potassium carbonate was added. This was designated as support WP-3.

(d) The same procedure was used as in paragraph (a) above but only 45 milliliters of water was added to 200 grams of potassium carbonate to produce the thick paste. The resulting material was designated as support WP-4.

Example II

Melt Process $K_2CO_3/Al_2O_3$ (a) Potassium carbonate on α-alumina

Ten grams of potassium carbonate was dissolved in 15 milliliters of water, added to 50 grams of α-alumina (Norton SA-5123, containing 87% alumina-11% silica; 8-20 mesh), allowed to stand for 15 minutes, concentrated in a film evaporator and then dried in a furnace at 500° C. for 3 hours. This material was designated as support MP-1.

(b) The same procedure used in paragraph (a) immediately above was repeated except that the temperature used to dry the potassium carbonate on alumina was changed to four 30 minute segments at 300°, 500°, 700° and 950° C. The resulting material was designated as support MP-2.

(c) Procedure used in paragraph (b) immediately above was repeated except that the α-alumina used was Norton SA-5102 (99% alumina). This material was designated as support MP-3.

(d) The procedure used in Example II paragraph (a) above was repeated except that Girdler T-1370 γ-alumina was used. The resulting material was designated as support MP-4.

B. CATALYST PREPARATION

Example III

Catalysts Using $K_2CO_3$ Support

Control Catalyst: $K-K_2CO_3$

Fifty grams of potassium carbonate ($K_2CO_3$) as received from Mallinckrodt, Inc. was screened to 16-30 mesh, and heated to 250° C. and then cooled to 80° C. and 2.5 grams (4.8 wt. %) of elemental potassium was added and dispersed with agitation. All processes of this type involving elemental potassium were carried out in a dry box under a nitrogen atmosphere.

Invention Catalyst A: $K-Cu-K_2CO_3$

The procedure used for the preparation of Control Catalyst was repeated except that after the elemental potassium (4.4 wt. %) was dispersed on the potassium carbonate support, then 4 grams (7.1 wt. %) of 300 mesh copper was added and dispersed with agitation.

Invention Catalyst B: $K-Cu-Co-K_2CO_3$

The procedure used for the preparation of Invention Catalyst A was repeated except that instead of adding 4 grams of powdered copper, a mixture of 2 grams (3.5 wt. %) of powdered copper and 2 grams (3.5 wt. %) of powdered cobalt was added with agitation.

Example IV

Catalysts Using $K_2CO_3$ Wet Process Support

Invention Catalyst C: $K-Cu-K_2CO_3$

The procedure used for the preparation of Invention Catalyst A was repeated except that support WP-1 (wet process $K_2CO_3$) was used.

Invention Catalyst D: $K-Cu-K_2CO_3$

The procedure used for the preparation of Invention Catalyst C was repeated except that 4.0 grams (6.9 wt. %) of elemental potassium was used. The resulting catalyst also contained 6.9 wt. % elemental copper based on total catalyst weight.

Invention Catalyst E: $K-Cu-K_2CO_3$

The procedure used for the preparation of Invention Catalyst D was repeated except that support WP-2 (wet process potassium carbonate) was used.

Invention Catalyst F: $K-Cu-K_2CO_3$

The procedure used for the preparation of Invention Catalyst C was repeated except that support WP-3 (wet process $K_2CO_3$) was used.

Invention Catalyst G: $K-Cu-K_2CO_3$

The procedure used for the preparation of Invention Catalyst C was repeated except that support WP-4 (wet process $K_2CO_3$) was used.

Example V

Catalysts on $K_2CO_3/Al_2O_3$ Supports

Invention Catalyst H

Potassium (2.5 grams; 4.4 wt. %) was added to 50 grams of support MP-1 ($K_2CO_3/\alpha$-$Al_2O_3$ which had been heated to 250° C. and then cooled to 85° C.). As the potassium melted, the container was shaken to disperse the potassium on the $K_2CO_3/Al_2O_3$. Then 4 grams (7.1 wt. %) of copper powder was added with agitation to distribute the copper on the $K/K_2CO_3/Al_2O_3$.

Invention Catalyst I

The procedure used for the preparation of Catalyst H was repeated except that support MP-2 was used.

Invention Catalyst J

The procedure used for the preparation of Catalyst H was repeated except that support MP-3 was used.

Invention Catalyst K

The procedure used for the preparation of Catalyst H was repeated except that support MP-4 was used.

Example VI

Catalysts on $K_2CO_3$ Containing Stainless Steel

Invention Catalyst L

Fifty grams of potassium carbonate as received from Mallinckrodt, Inc., screened to 16-30 mesh) was heated to 250° C. in a round bottom flask under an inert atmosphere, cooled to 85° C. after which 2.5 grams of potassium were added, allowed to melt and dispersed with agitation. Four grams of 325 mesh 316 stainless steel (SS) powder was added with agitation and the mixtures was cooled under an inert atmosphere.

Invention Catalyst M

The procedure used for the preparation of Catalyst L was repeated except that 20 grams of SS was used.

Invention Catalyst N

The procedure used for the preparation of Catalyst L was repeated except that 10 grams of 100 mesh SS was used.

Invention Catalyst O

The procedure used for the preparation of Catalyst L was repeated except that 20 grams of 100 mesh SS was used.

Invention Catalyst P

The procedure used for the preparation of Catalyst L was repeated except that 25 grams of 100 mesh SS was used.

Invention Catalyst Q

The procedure used for the preparation of Catalyst L was repeated except that 20 grams of 303 SS was used.

Invention Catalyst R

The procedure used for the preparation of Catalyst L was repeated except that 20 grams of 410 SS was used.

Invention Catalyst S

The procedure used for the preparation of Catalyst L was used except that 20 grams of 431 SS was used.

Invention Catalyst T

The procedure used for the preparation of Catalyst L was used except that 20 grams of cobalt powder was used instead of SS.

Comparison Catalyst U

The procedure used for the preparation of Catalyst L was used except that 20 grams of 20–45 mesh nickel powder was used.

Invention Catalyst V

The procedure used for the preparation of Catalyst L was used except that 20 grams of 304 SS was used.

Example VII

Dimerization of Propylene

Typically, the dimerization of propylene was carried out in a steam heated 316 stainless steel tubular reactor ($\frac{1}{2}'' \times 20''$). The catalyst (40 mL), bounded above and below by small volumes of glass beads, was heated to the desired reaction temperature at about 2000 psig and the propylene was pumped into the reactor at a rate of about 60 mL/hr. After about 20 hours of reaction time a sample was taken and any desired temperature changes were made, the operation continued for an additional 5–10 hours and another sample was taken and analyzed.

Table I shows results obtained with $K_2CO_3$ supported catalysts, prepared as described in Example III.

TABLE I

Dimerization of Propylene Using $K_2CO_3$ Support

| Run No. | Catalyst | Metal* K, % | Cu, % | Co, % | Temp., °C. | Propylene Conv., % | Selectivity to 4MP1** |
|---|---|---|---|---|---|---|---|
| 1 | Control | 4.8 | 0 | 0 | 150 | 51 | 77 |
| 2 | Invention A | 4.4 | 7.1 | 0 | 150 | 53 | 85 |
| 3 | Invention B | 4.4 | 3.5 | 3.5 | 150 | 68 | 83 |

*Metal content shown as % of total catalyst weight.
**4-methyl-1-pentene.

The addition of copper (7.1 wt. %) to the K-$K_2CO_3$ catalyst (producing Invention Catalyst A) improves both the conversion of propylene and the selectivity to the dimeric 1-isomer, 4-methyl-1-pentene. The addition of a mixture of copper (3.5 wt. %) and cobalt (3.5 wt. %) gives further improvement in the propylene conversion and comparable selectivity to 4-MP-1.

Example VIII

Dimerization of Propylene Using Wet Process $K_2CO_3$ Supported Catalysts.

For some applications, such as fixed-bed reactors, it would be advantageous to have catalyst particle sizes larger than the approximately 12–80 mesh normally obtained commercially. Smaller particles could cause excessive pressure drop through the bed in such reactors. Larger particles were obtained by mixing water with the potassium carbonate as described in Example I for the preparation of the catalyst support by the wet process. The $K_2CO_3$ was screened to recover an 8–14 mesh fraction for use in the laboratory fixed bed reactor. The effects on catalyst performance resulting from the variations of treatment to obtain larger particles was surprising as shown in Table II. All runs tabulated in the table were carried out at 2000 psig and a propylene flow of 60 mL/hr.

TABLE II

Effects of "Wet Process" Modifications of $K_2CO_3$ Support on Catalyst Performance

| Run No. | Catalyst No. | Mesh Size | Metal* k, % | Cu, % | Rxn. Temp., °C. | Propylene Conv., % | 4MP1 Sel., % | 4MP1 4MP2 |
|---|---|---|---|---|---|---|---|---|
| 4 | Invention A | 16/30 | 4.4 | 7.1 | 140 | 33 | 87 | 29 |
|   |   |   |   |   | 150 | 53 | 85 | 18 |
| 5 | Invention C | 8/14 | 4.4 | 7.1 | 140 | 11 | 79 | 21 |
|   |   |   |   |   | 150 | 20 | 80 | 14 |
| 6 | Invention F | 8/14 | 4.4 | 7.1 | 140 | 23 | 87 | 34 |
|   |   |   |   |   | 150 | 37 | 85 | 24 |
| 7 | Invention G | 8/14 | 4.4 | 7.1 | 140 | 21 | 86 | 42 |
|   |   |   |   |   | 150 | 38 | 97 | 28 |
| 8 | Invention D | 8/14 | 6.9 | 6.9 | 140 | 19 | 81 | 16 |
|   |   |   |   |   | 150 | 30 | 79 | 12 |
| 9 | Invention E | 8/14 | 6.9 | 6.9 | 140 | 46 | 85 | 23 |
|   |   |   |   |   | 150 | 67 | 83 | 13 |

*Metal content shown as % of total catalyst weight.

The support employed to prepare Invention Catalyst C was prepared by simply adding enough water to potassium carbonate to form a moderately thick paste, heating in an oven to remove water, followed by grinding and screening. Lower propylene conversions along with slightly lower selectivities and olefin isomer ratios (1-olefin:2-olefin) were obtained than in the run employing Invention Catalyst A (Run 4). Run 6 employing Invention Catalyst F shows the importance of the technique used to prepare the granular K₂CO₃. Again, water and potassium carbonate were mixed to form a paste; then enough additional K₂CO₃ was added to give a very thick, lumpy material; the paste was dried, granulated and used as the support for the preparation of a dimerization catalyst containing 4.4 wt. % K and 7.1% wt. % Cu. Both olefin isomer ratios and product selectivities were comparable to those obtained with Invention Catalyst A. In Run 7 employing Invention Catalyst G, support was prepared by adding just enough water to the potassium carbonate to give directly the same type of thick, lumpy paste obtained in the preparation of catalyst employed in run 6. Invention Catalyst G prepared from this support gave essentially the same results as obtained with Invention Catalyst F employed in run 6. Run 8 employing Invention Catalyst D shows that a catalyst based on the same wet process support used for the preparation of catalyst employed in run 6 but containing 6.9 wt. % K and 6.9 wt. % Cu resulted in lower olefin isomer ratios, selectivities and conversions than obtained with Invention Catalysts A, F and G which each had lower elemental potassium loading. When the support was prepared by forming a moderately thick paste and then adding additional potassium carbonate in small portions to form a very thick paste as described in Example I, support WP-2, and then adding 6.9 wt. % Cu to give Invention Catalyst E as employed in run 9, olefin isomer ratios and selectivities were roughly comparable to those obtained with Invention Catalyst A (Run 4) and the propylene conversions were much higher.

Example IX

Dimerization of Propylene Using K₂CO₃/Al₂O₃ Supported Catalysts

It is desirable under some circumstances to have a more durable catalyst for propylene dimerization than that provided by a granular potassium carbonate support. The fragility of the granular potassium carbonate can lead to the development of fines and subsequent plugging in a continuous reactor. Potassium on a support such as alumina does not provide satisfactory catalytic activity for dimerization of propylene. By impregnating an α-alumina (86%)-silica (11%) with an aqueous solution of potassium carbonate as described in Example II followed by the addition of potassium and optionally other catalytic materials, as described in Example V, a more durable catalyst is obtained. Table III summarizes results obtained by the use of this type of catalyst. All runs tabulated below were carried out at 2000 psig and a propylene flow of 60 mL/hr. All catalysts differed only in the nature of the support, each having 4.4 wt. % elemental potassium and 7.1 wt. % elemental copper.

TABLE III

K₂CO₃/Al₂O₃ Supported Catalysts for Dimerization of Propylene

| Run No. | Catalyst | Temp., °C. | Conv., % | 4MP1 Sel., % | 4MP1 4MP2 |
|---|---|---|---|---|---|
| 10 | Invention A | 140 | 33 | 87 | 29 |
|  |  | 150 | 53 | 85 | 18 |
| 11 | Invention H | 140 | 15 | 79 | 11 |
|  |  | 150 | 24 | 79 | 8 |
| 12 | Invention I | 140 | 33 | 86 | 20 |
|  |  | 150 | 64 | 79 | 10 |
| 13 | Invention J | 140 | 29 | 81 | 9 |
|  |  | 150 | 26 | 78 | 6 |
| 14 | Invention K | 140 | 43 | (*) | <1 |
|  |  | 150 | 53 | (*) | <1 |

*Major product 2-methyl-2-pentene (approximately 65% selectivity)

Heating the K₂CO₃/α-Al₂O₃ combination only to 500° C. before adding the elemental potassium and elemental copper (Catalyst H; Run 11), produced lower conversion and selectivity than obtained with Catalyst A employing the K₂CO₃ alone as support (Run 10). Where the K₂CO₃/α-Al₂CO₃ was heated to 950° C. (Catalyst I; Run 12), at which point the K₂CO₃ is molten, the results are comparable to those obtained with Catalyst A (Run 10).

The type of alumina employed is also shown to be important. A support of K₂CO₃/α-Al₂O₃ (99%) (Catalyst J; Run 13) gives lower propylene conversion than an α-Al₂O₃ comprising about 87% α-Al₂O₃ and 11% SiO₂. The use of γ-Al₂O₃ gives 2-methylpentene-2 as the major product (Catalyst K; Run 14), which probably arises by the isomerization of the primary reaction product, 4-methyl-1-pentene.

Example XII

Dimerization of Propylene using Stainless Steel Containing K₂CO₃ Support

Another approach to increasing the durability of dimerization catalyst is through the addition of metal particles in amounts sufficient to provide the desired durability. One preferred metal for this application is 316 stainless steel. The amount, mesh size and type of metal each play a part in the effectiveness of the resulting catalyst.

Table IV shows the effects of changing the stainless steel loading and mesh size on the catalyst durability and performance in the propylene dimerization. All runs were carried out at 2000 psig and a propylene flow of 60mL/hr.

TABLE IV

Effect of Stainless Steel Loading on Catalyst Durability

| Run No. | Catalyst | Metal* K, % | Metal* SS, % | Mesh | Rxn. Temp., °C. | Catalyst Condition After 30 hrs | Conv., % | Sel., % | 4MP1 4MP2 |
|---|---|---|---|---|---|---|---|---|---|
| 15 | Invention L | 4.4 | 7.1 | 325 | 140 | Moderate | 32 | 87 | 28 |
|  |  |  |  |  | 150 | Plugging | 50 | 84 | 17 |
| 16 | Invention M | 3.4 | 27.5 | 325 | 140 | Slight | 31 | 86 | 25 |
|  |  |  |  |  | 150 | Plugging | 46 | 85 | 17 |
| 17 | Invention N | 4 | 16 | 100 | 140 | Slight | 33 | 87 | 27 |
|  |  |  |  |  | 150 | Plugging | 45 | 84 | 18 |
| 18 | Invention O | 3.4 | 27.5 | 100 | 140 | No | 36 | 86 | 27 |
|  |  |  |  |  | 150 | Plugging | 50 | 84 | 17 |
| 19 | Invention P | 3.2 | 32.3 | 100 | 140 | No | 25 | 85 | 19 |
|  |  |  |  |  | 150 | Plugging | 38 | 84 | 13 |

*Metal content shown as % of total catalyst weight

Increasing the amount of 325 mesh stainless steel (SS) from 7.1 wt. % (Run 15) to 27.5 wt. % (Run 16) improves the catalyst stability with respect to reactor plugging. Only a slight crust forms on the top of the bed with little change noted otherwise in the results over a 30-hour run period. Using a large particle size SS (100 mesh) at the level of about 16 wt. % (Catalyst N; Run 17) gives results comparable to those obtained with a greater loading (27.5 wt. %) of smaller particle size SS(325 mesh; Catalyst M; Run 16). At the level of about 27.5 wt. % of 100 mesh 316 SS(Catalyst O; Run 18) reaction results are comparable to those obtained with the same loading level of 325 mesh SS(Catalyst M; Run 16), with essentially no reactor plugging observed over a 30-hour evaluation. Using greater than 30 wt. % level of 100 mesh SS (Catalyst P; Run 19) shows no advantage over 27.5 wt. % (Catalyst O; Run 18).

Example XI

Dimerization of Propylene Using Metal-Containing $K_3CO_3$ Support

The effect on catalyst activity of various stainless steels, as well as other metals, was investigated. Results are summarized in Table V. In all reactions, reactor pressure was 2000 psig, propylene flow rate 60 mL/hr. Each catalyst employed had about 3.4 wt. % elemental potassium and about 27.5 wt. % added metal.

TABLE V

Effect of Metal type on Propylene Dimerization Results

| Run No. | Catalyst | Metal Type | Rxn. Temp., C. | Conv., % | Sel., % | 4MP1 4MP2 |
|---|---|---|---|---|---|---|
| 20 | Invention O | 316 SS | 140 | 36 | 86 | 27 |
|   |   |   | 150 | 50 | 84 | 17 |
| 21 | Invention Q | 303 SS | 140 | 27 | 84 | 22 |
|   |   |   | 150 | 42 | 83 | 15 |
| 22 | Invention R | 410 SS | 140 | 21 | 82 | 17 |
|   |   |   | 150 | 34 | 81 | 12 |
| 23 | Invention S | 431 SS | 140 | 30 | 85 | 25 |
|   |   |   | 150 | 48 | 83 | 14 |
| 24 | Invention T | Cobalt | 140 | 24 | 82 | 19 |
|   |   |   | 150 | 36 | 81 | 13 |
| 25 | Comparison U | Nickel | 140 | 25 | 80 | 14 |
|   |   |   | 150 | 33 | 80 | 10 |

In Table V, Runs 20–23 demonstrate that the type of metal used has an effect on the dimerization results. The 303, 410 and 431 stainless steels, for example, produce lower conversion, selectivities and olefin ratios than does 316SS. Catalyst durability was good in each case. The nickel (Run 25) is an example of another metal that will function in the place of the SS but not as effectively as the SS under the reaction conditions used.

Example XII

Codimerization of Ethylene and Propylene

The procedure employed for the dimerization of propylene (Example VII) was repeated except that 34 g/hour of ethylene and 31 g/hour of propylene were added to the reactor. The amount of potassium and potassium carbonate was the same in both catalysts. The results are shown in Table VI.

TABLE VI

| | | | Codimerization of Ethylene and Propylene Product Sel, % | | | | | |
|---|---|---|---|---|---|---|---|---|
| Run No. | Catalyst | Temp. °C. | Ethylene | Propylene | 1-Pentene | 2-Pentene | Others | 1-Pentene 2-Pentene |
| 26 | Invention V | 155 | 21.5 | 25.1 | 44.5 | 2.12 | 7.4 | 21.0 |
|   |   | 135 | 18.9 | 23.5 | 44.6 | 1.9 | 11.2 | 23.5 |
| 27 | Control | 156 | 25.7 | 4.4 | 44.6 | 3.3 | 22.0 | 13.5 |

When the stainless steel was put in the catalyst system, there was less tendency to form fines that lead to plugging and the reaction was more selective toward the formation at 1-pentene. Much less propylene dimer was formed, accounting for the lower conversion of propylene.

I claim:

1. A catalyst consisting essentially of:
   (a) at least one alkali metal,
   (b) elemental copper, and
   (c) potassium carbonate support; wherein components (a) and (b) are supported on component (c).

2. A catalyst consisting essentially of:
   (a) at least one alkali metal, (b) elemental copper, (c) elemental cobalt, and (d) potassium carbonate support; wherein components (a), (b) and (c) are supported on component (d).

3. A catalyst consisting essentially of:
   (a) at least one alkali metal, (b) elemental copper, (c) finely divided stainless steel, and (d) potassium carbonate support; wherein components (a), (b) and(c) are supported on component (d).

4. A catalyst in accordance with claim 1 wherein said components are present in the amounts of about:
   1–20 wt. % of at least one elemental alkali metal, and
   1–30 wt. % elemental copper based on total weight of (a), (b) and (c).

5. A catalyst in accordance with claim 2 wherein said components are present in the amounts of about:
   1–20 wt. % of at least one elemental alkali metal,
   1–30 wt. % elemental copper, and
   1–50 wt. % elemental cobalt based on total weight of (a), (b), (c) and (d).

6. A catalyst in accordance with claim 3 wherein said components are present in the amount of about:
   1–20 wt. % of at least elemental alkali metal,
   1–30 wt. % elemental copper, and
   1–80 wt. % finely divided stainless steel based on total weight of (a), (b), (c) and (d).

7. A catalyst in accordance with claim 4 wherein at least one elemental alkali metal is elemental potassium.

8. A catalyst in accordance with claim 5 wherein at least one elemental alkali metal is elemental potassium.

9. A catalyst in accordance with claim 6 wherein at least one elemental alkali metal is elemental potassium.

10. A catalyst consisting essentially of:
    (a) at least one elemental alkali metal,
    (b) finely divided stainless steel, and
    (c) potassium carbonate support; wherein components (a) and (b) are supported on component (c).

11. A catalyst in accordance with claim 10 wherein said components are present in the amount of about:
    16–20 wt. % of at least one elemental alkali metal, and 1-80 wt. % finely divided stainless steel based on total weight of (a), (b) and (c).

12. A catalyst in accordance with claim 11 wherein said at least one elemental alkali metal is elemental potassium.

13. A catalyst in accordance with claim 1 wherein said potassium carbonate support has been prepared by (i) adding sufficient water to potassium carbonate to form a thick paste, (ii) drying said thick paste, and (iii) crushing the dried paste into the desired particle size for treatment of the potassium carbonate support with components (a) and (b).

14. A catalyst in accordance with claim 2 wherein said potassium carbonate support has been prepared by (i) adding sufficient water to potassium carbonate to form a thick paste, (ii) drying said thick paste, and (iii) crushing the dried paste into the desired particle size for treatment of the potassium carbonate support with components (a), (b) and (d).

15. A catalyst in accordance with claim 10 wherein said potassium carbonate support has been prepared by (i) adding sufficient water to potassium carbonate to form a thick paste, (ii) drying said thick paste, and (iii) crushing the dried paste into the desired particle size for treatment of the potassium carbonate support with components (a) and (b).

16. A catalyst consisting essentially of:
(a) at least one alkali metal, and
(b) a mixed potassium carbonate, alpha-alumina support; wherein said potassium carbonate and said alpha-alumina of said mixed potassium carbonate, alpha-alumina support are present in a weight ratio in the range of about 1:1 to 1:10 potassium carbonate/alpha-alumina.

17. A catalyst in accordance with claim 16 wherein said at least one elemental alkali metal is elemental potassium.

18. A catalyst consisting essentially of:
(a) at least one alkali metal,
(b) elemental copper, and
(c) a mixed potassium carbonate, alpha-alumina support; wherein said potassium carbonate and said alpha-alumina of said mixed support are present in a weight ratio in the range of about 1:1 to 1:10 potassium carbonate/alpha-alumina.

19. A catalyst consisting essentially of:
(a) at least one elemental alkali metal,
(b) elemental copper,
(c) elemental cobalt, and
(d) a mixed potassium carbonate, alpha-alminum support; wherein said potassium carbonate and said alpha-alumina of said mixed support are present in a weight ratio in the range of about 1:1 to 1:10 potassium carbonate/alpha-alumina.

20. A method for the preparation of catalyst comprising:
(a) heating a mixture of potassium carbonate and an alpha-alumina support to at least about 950° C.,
(b) cooling said mixture to about 80° to 100° C., and
(c) contacting the result of step (b) with at least one alkai metal.

21. A method according to claim 20 further comprising:
(d) contacting the result of step (c) with one or more components selceted from the group consisting of:
elemental copper,
elemental cobalt,
finely divided stainless steel, and mixtures of any two or more thereof.

22. A method according to claim 21 wherein said at least one elemental alkali metal is elemental potassium.

23. A method according to claim 21 wherein said at least one elemental alkali metal is elemental potassium.

24. A method for the preparation of catalyst comprising:
(a) preparing a thick paste comprising potassium carbonate and water admixed in weight ratio fo at least 3.5:1;
(b) drying under conditions cuitable to remove essentially all the water from said paste;
(c) crushing the dried product of step (b);
(d) collecting a uniform particle size fraction;
(e) contacting said uniform particle sixe fraction with at least one elemental alkali metal;
(f) contacting the result of step (e) with one or more components selected from the group consisting of:
elemental copper,
elemental cobalt,
finely divided stainless steel, and mixtures of any two or more thereof.

25. A method according to claim 24 wherein said at least one elemental alkali metal is elemental potassium.

* * * * *

UNITED STATES PATENT AND TRADEMARK OFFICE
CERTIFICATE OF CORRECTION

PATENT NO. : 4,609,637
DATED : 9/2/86
INVENTOR(S) : Charles A. Drake

It is certified that error appears in the above—identified patent and that said Letters Patent are hereby corrected as shown below:

Col. 14, line 68, "16-20" should read ---1-20---.
Col. 16, line 19, "selceted" should read ---selected---.
Col. 16, line 31, insert "a" after ---in--- and before ---weight---.
Col. 16, line 31, "fo" should read ---of---.
Col. 16, line 33, "cuitable" should read ---suitable---.
Col. 16, line 37, "sixe" should read ---size---.

Signed and Sealed this

Sixth Day of January, 1987

Attest:

DONALD J. QUIGG

Attesting Officer

Commissioner of Patents and Trademarks